United States Patent
Mabold

(10) Patent No.: US 11,963,803 B2
(45) Date of Patent: Apr. 23, 2024

(54) OMMAYA RESERVOIR TRAY FOR INSTALLATION OF INTRAVENTRICULAR CHEMOTHERAPY AND/OR ASPIRATION OF CEREBROSPINAL FLUID FOR DIAGNOSTIC PURPOSES

(71) Applicant: Jennifer Mabold, Evans City, PA (US)

(72) Inventor: Jennifer Mabold, Evans City, PA (US)

(*) Notice: Subject to any disclaimer, the term of this patent is extended or adjusted under 35 U.S.C. 154(b) by 548 days.

(21) Appl. No.: 17/360,405

(22) Filed: Jun. 28, 2021

(65) Prior Publication Data
US 2022/0409322 A1 Dec. 29, 2022

(51) Int. Cl.
| | |
|---|---|
| *A61M 5/00* | (2006.01) |
| *A61B 46/20* | (2016.01) |
| *A61B 50/33* | (2016.01) |
| A61B 10/00 | (2006.01) |
| A61F 15/00 | (2006.01) |
| A61M 25/06 | (2006.01) |
| A61M 39/22 | (2006.01) |

(52) U.S. Cl.
CPC ............. *A61B 50/33* (2016.02); *A61B 46/20* (2016.02); *A61M 5/002* (2013.01); *A61B 2010/0077* (2013.01); *A61F 15/001* (2013.01); *A61M 25/0637* (2013.01); *A61M 2039/229* (2013.01)

(58) Field of Classification Search
CPC . A61B 50/33; A61B 46/20; A61B 2010/0077; A61M 5/002; A61M 25/0637; A61M 2039/229; A61F 15/001

USPC .......................................................... 206/570
See application file for complete search history.

(56) References Cited

U.S. PATENT DOCUMENTS

| | | | |
|---|---|---|---|
| 6,946,134 B1* | 9/2005 | Rosen ................. | C07K 14/765 435/7.1 |
| 11,213,365 B1* | 1/2022 | Angelillo ............... | A61B 50/33 |
| 2016/0228676 A1* | 8/2016 | Glithero ................. | A61B 50/20 |
| 2017/0049989 A1* | 2/2017 | Kapural ................ | A61M 5/162 |
| 2020/0375745 A1* | 12/2020 | Sampath ............... | A61F 2/2875 |
| 2022/0009657 A1* | 1/2022 | Tomes ................ | A61M 25/002 |
| 2022/0016338 A1* | 1/2022 | Abrams ............ | A61M 5/14276 |
| 2022/0062614 A1* | 3/2022 | Pittman ................. | A61M 39/02 |

* cited by examiner

*Primary Examiner* — Jacob K Ackun
(74) *Attorney, Agent, or Firm* — The Rapacke Law Group, P.A.; Andrew S. Rapacke

(57) ABSTRACT

A number of variations may include a sterile kit that may include a tray constructed and arranged to hold the necessary items to access an Ommaya reservoir and the tray may define a plurality of other resources or indentations constructed and arranged to seat, hold, or house additional components of the sterile kit. The sterile kit may additionally include a paper towel, a fenestrated drape, a plurality of sponge applicators, at least one pouch of povidone-iodine, at least one retractable winged butterfly needle, at least one luer lock syringe, a 3-way stopcock, a plurality of collection vials with tops which may be screwed on to prevent the contents thereof from leaking or escaping, sterile pads, bandages including adhesive bandages, and other components.

20 Claims, 2 Drawing Sheets

OMMAYA RESERVOIR TRAY FOR INSTALLATION OF INTRAVENTRICULAR CHEMOTHERAPY AND/OR ASPIRATION OF CEREBROSPINAL FLUID FOR DIAGNOSTIC PURPOSES

TECHNICAL FIELD

The field to which the disclosure generally relates includes accessing an Ommaya reservoir to obtain cerebrospinal (CSF) for diagnostic purposes and/or for administering intraventricular chemotherapy.

BACKGROUND

The present disclosure relates to a kit and method for accessing an Ommaya reservoir to obtain CSF for diagnostic purposes and/or for administering intraventricular chemotherapy. When obtaining CSF or administrating intraventricular chemotherapy via an Ommaya reservoir, a health care professional may traditionally utilize a lumbar puncture tray or kit. A lumbar puncture tray or kit may contain numerous items or tools not needed for accessing an Ommaya reservoir. As a non-limiting example, in lumbar puncture tray or kit may include unnecessary items and tools such as utility markers, monometer tubes, monometers, extension lines, filter straws, spinal needles with stylets, needle receptacles, and other items. Additionally, lumbar puncture trays or kits do not contain all of the tools necessary to access an Ommaya reservoir. As a non-limiting example, lumbar puncture kits commonly do not include retractable butterfly needles which are required to access an Ommaya reservoir to obtain CSF or administer interventricular chemotherapy.

SUMMARY

This summary is provided to introduce a variety of concepts in a simplified form that is further disclosed in the detailed description of the embodiments. This summary is not intended to identify key or essential inventive concepts of the claimed subject matter, nor is it intended for determining the scope of the claimed subject matter.

A sterile kit may include a tray constructed and arranged to hold the necessary items to access an Ommaya reservoir. The tray may be wrapped in medical grade sterile paper or sealed such that the contents remained sterile while opening the tray and using the contents therein. The tray may define at least four indentations constructed and arranged to seat collection vials such that the collection vials may stand upright with lids open. As a non-limiting example, the tray may define at least four indentations to seat four 8 cc collection vials in an upright position such that when CSF is collected it may be deposited in the upright collection vials in a sterile and time effective manner.

A sterile kit may include a tray constructed and arranged to hold the necessary items to access an Ommaya reservoir and the tray may define a plurality of other resources or indentations constructed and arranged to seat, hold, or house additional components of the sterile kit. The sterile kit may additionally include a paper towel, a fenestrated drape, a plurality of sponge applicators, at least one pouch of povidone-iodine, at least one retractable winged butterfly needle, at least one luer lock syringe, a 3-way stopcock, a plurality of collection vials with tops which may be screwed on to prevent the contents thereof from leaking or escaping, sterile pads, bandages including adhesive bandages, and other components.

A method of accessing an Ommaya reservoir to obtain CSF and/or for administering intraventricular chemotherapy with an Ommaya reservoir kit including a sealed tray constructed and arranged to contain a fenestrated drape, a sponge applicator, a container of povidone-iodine, a retractable winged butterfly needle, a luer lock syringe, a 3-way stopcock, a sealable collection vial, and a sterile gauze pad. The method may include the following steps: opening the sealed tray; opening the container of povidone-iodine pouch and pouring the contents of the povidone-iodine pouch into a recessed portion of the tray; utilizing the sponge applicator to cleanse a patients Ommaya reservoir by dipping the applicator sponge in povidone-iodine and cleansing a patients Ommaya reservoir in a circular motion; removing the fenestrated drape from the kit and placing the fenestrated drape over the Ommaya reservoir to create a sterile field over the patient; opening the sealable collection vial and positioning the sealable collection vial upright in a vial indentation defined by the tray; removing the retractable winged butterfly needle from the kit; positioning the retractable winged butterfly needle approximately perpendicular to the skin of a patient to access the Ommaya reservoir; removing the luer lock syringe from the kit; connecting the luer lock syringe to the retractable winged butterfly needle; drawing a volume of CSF from the Ommaya reservoir; and injecting the CSF into the upright sealable collection vial.

Additional features and advantages of the embodiments disclosed herein will be set forth in the detailed description that follows, and in part will be clear to those skilled in the art from that description or recognized by practicing the embodiments described herein, including the detailed description which follows, the claims, as well as the appended drawings.

Both the foregoing general description and the following detailed description present embodiments intended to provide an overview or framework for understanding the nature and character of the embodiments disclosed herein. The accompanying drawings are included to provide further understanding and are incorporated into and constitute a part of this specification. The drawings illustrate various embodiments of the disclosure, and together with the description explain the principles and operations thereof.

BRIEF DESCRIPTION OF THE DRAWINGS

The features and advantages of the present disclosure will be more fully described in, or rendered obvious by the following detailed description of the preferred embodiments, which are to be considered together with the accompanying drawings wherein like numbers refer to like parts and further, wherein.

DETAILED DESCRIPTION

Figure 1:
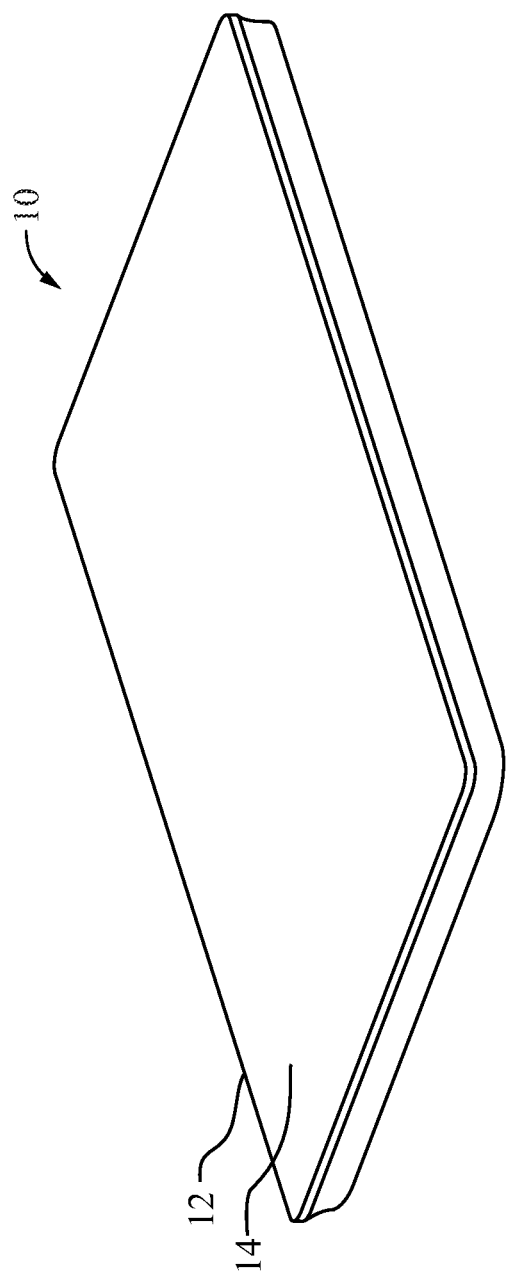
FIG. 1 is a perspective view of a kit for accessing an Ommaya reservoir to obtain CSF for diagnostic purposes and/or for administering intraventricular chemotherapy.

Reference will now be made in detail to the present preferred embodiment(s), and examples of which is/are illustrated in the accompanying drawings. Whenever possible, the same reference numerals will be used throughout the drawings to refer to the same or like parts. Any specific details of the embodiments are used for demonstration purposes only, and no unnecessary limitations or inferences are to be understood therefrom.

The following description of the variations is merely illustrative in nature and is in no way intended to limit the scope of the invention, its application, or uses. The following description of variants is only illustrative of components, elements, acts, products, and methods considered to be within the scope of the invention and are not in any way intended to limit such scope by what is specifically disclosed or not expressly set forth. The components, elements, acts, products, and methods as described herein may be combined and rearranged other than as expressly described herein and still are within the scope of the invention.

A kit and method for accessing an Ommaya reservoir to obtain CSF for diagnostic purposes and/or for administering intraventricular chemotherapy may improve medical facility cost effectiveness by reducing the reliance upon lumbar puncture tray or kits and the unnecessary disposal of unused tools when accessing an Ommaya reservoir. Additionally, the kit and method disclosed herein may increase convenience and effectiveness of health care providers and professionals performing the process of obtaining CSF or administering interventricular chemotherapy. A kit and method disclosed herein may also reduce storage costs, reduce shipping costs, and streamline the process of obtaining CSF or administering intraventricular chemotherapy via an Ommaya reservoir by reducing reliance on medical devices and kits not specifically designed for the processes and procedures associated with the accessing an Ommaya reservoir.

A sterile kit may include a tray constructed and arranged to hold the necessary items to access an Ommaya reservoir. The tray may be wrapped in medical grade sterile and sealed such that the contents remain sterile while opening the tray and using the contents therein. The tray may define at least 4 indentations constructed and arranged to seat collection vials both in a prone, approximately horizontal position as well as an upright, vertical position such that the collection vials may stand upright with lids open. Alternatively, the tray may define at least four indentations or channels constructed and arranged to seat collection vials in approximately horizontal position and four recesses constructed and arranged to seat collection files in approximately vertical position such that the collection vials may stand upright with lids open. As a non-limiting example, the tray may define at least four indentations to seat four 8 cc collection vials in an upright position such that when CSF is collected it may be deposited in the upright collection vials in a sterile and time effective manner.

Referring to FIG. 1, a kit 10 and method for accessing an Ommaya reservoir to obtain CSF for diagnostic purposes and/or for administering intraventricular chemotherapy may include a tray 12 wrapped in medical grade sterile paper 14 or sealed such that the contents of the kit remain sterile while opening the tray and using the contents therein. The tray 12 may be constructed and arranged to hold and at least partially contain the contents of the kit 10. The tray 12 may be made of, for example but not limited to, medical grade plastic or metal but other suitable materials are considered part of this disclosure. The medical grade sterile paper 14 or seal may be a top-sheet fixed to a top surface or edge of the tray 12 or film that full encapsulates the tray 12 and its contents.

Figure 2:
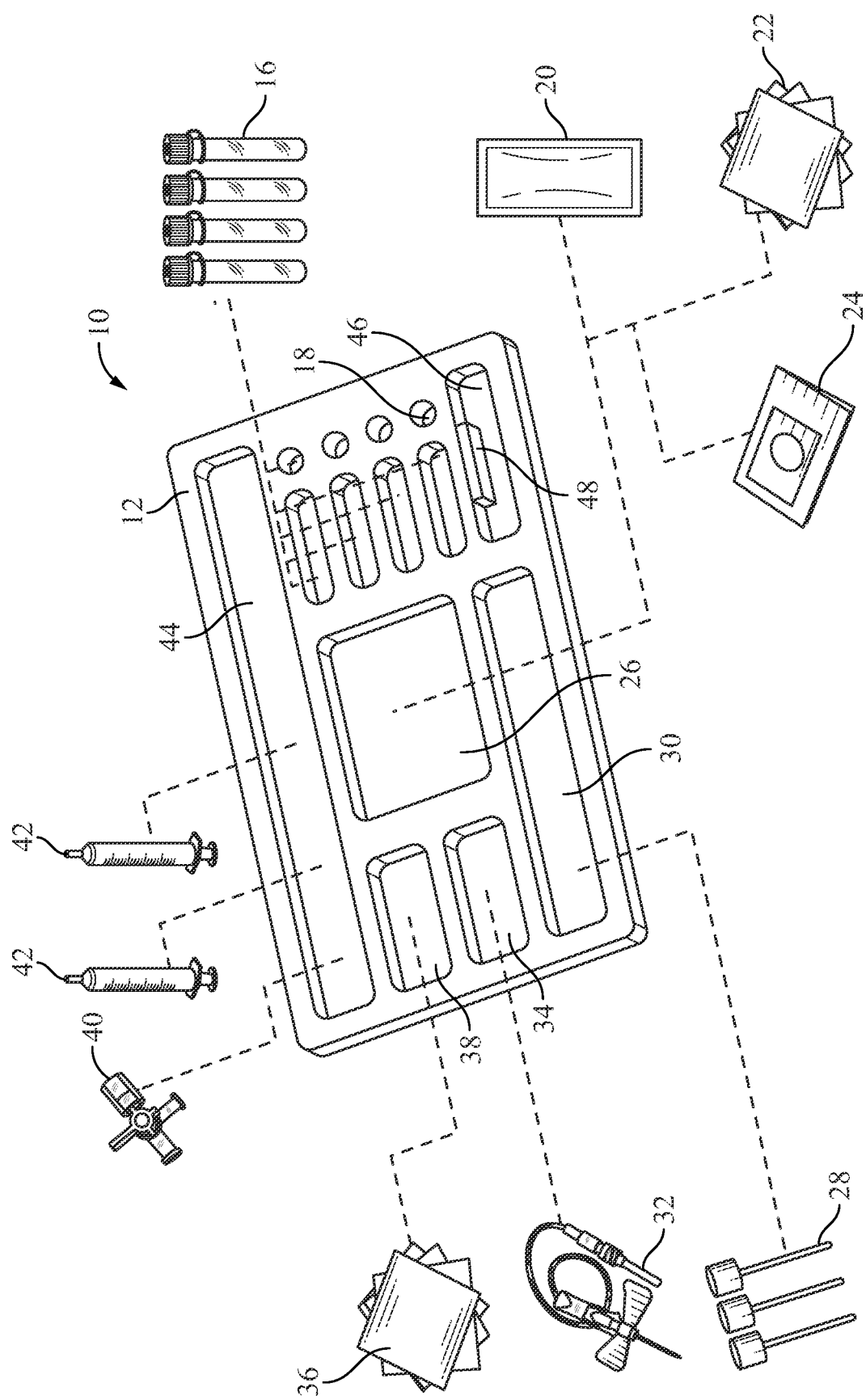
FIG. 2 is an exploded-perspective view of a kit for accessing an Ommaya reservoir to obtain CSF for diagnostic purposes and/or for administering intraventricular chemotherapy and a method of using said kit.

Referring to FIG. 2, a kit 10 and method for accessing an Ommaya reservoir to obtain CSF for diagnostic purposes and/or for administering intraventricular chemotherapy may include a tray 12 defining a plurality of indentations, recesses, channels, or the like for holding the contents of the kit 10. The tray 12 may define a plurality of collection vial recesses 18 constructed and arranged to seat the at least one sealable collection vial 16 in an approximately horizontal position and to seat the at least one sealable collection vial 16 in an approximately vertical position. The tray 12 may define a center recess 26 constructed and arranged to hold at least one container of povidone-iodine 20, at least one sterile towel 22, at least one fenestrated drape 24, and additional bandages such as adhesive bandages. The tray 12 may define a povidone-iodine recess 46 constructed and arranged to contain povidone-iodine. The povidone-iodine recess 46 may further include a blotter 48 constructed and arranged to assist in removing excess povidone-iodine from a sponge applicator 28. The tray 12 may define an applicator recess 30 constructed and arranged to hold at least one sponge applicator 28. The at least one sponge applicator 28 maybe a plurality of sponge applicators. The tray 12 may define a butterfly needle recess 34 constructed and arranged to hold at least one retractable winged butterfly needle 32. The tray 12 may define a gauze recess 38 constructed and arranged to hold at least one sterile gauze pad 36. The at least one sterile gauze pad 36 may include a plurality of sterile gauze pads. The tray 12 may define a syringe recess 44 constructed an arranged to hold at least one 3-way stopcock 40 and at least one luer lock syringe 42. The at least one luer lock syringe 42 may include a plurality of luer lock syringes.

In practice and in use, a method for accessing an Ommaya reservoir to obtain CSF for diagnostic purposes and/or for administering intraventricular chemotherapy may include providing a sterile Ommaya reservoir tray as described herein, opening the sterile Ommaya reservoir tray, removing a paper towel from the tray and placing the paper towel underneath the patient's head, opening a povidone-iodine pouch and pouring the contents of the povidone-iodine pouch into the povidone-iodine recess on the tray, utilizing the provided applicator sponges to cleanse a patients Ommaya reservoir by dipping an applicator sponge in povidone-iodine, using a raised blotter to remove excess povidone item and, in a circular motion starting in the center and working outwards, cleanse a patients Ommaya reservoir. A fenestrated drape may be removed from the kit and placed over the Ommaya reservoir to create a sterile field over the patient. Collection vials as provided in the kit may have their lids or caps removed and be placed in an upright position in indentations defined by the tray. A retractable winged butterfly needle, such as but not limited to, a 25-gauge butterfly needle, may be removed from the kit and positioned approximately perpendicular to the skin of a patient to access the Ommaya reservoir. A luer lock syringe may be removed from the kit and connected to the winged butterfly needle. A desired volume of CSF may be drawn from the Ommaya reservoir and injected into the awaiting upright collection vials. The sterile kit may provide for a plurality of luer lock syringes such that the desired volume of CSF may be drawn by filling a first luer lock syringe with CSF and replacing it with a subsequent luer lock syringe and repeating the process as needed. Once filled, the upright collection vials may be capped or sealed. Optionally after collection of CSF is complete, a 3-way stopcock may be securely attached to the winged butterfly needle to assist in administering chemotherapy followed by preservative normal saline flush. The winged butterfly needle may be removed, and light pressure may be placed on the Ommaya reservoir with a sterile gauze as provided in the kit. An adhesive bandage may be applied over the injection site.

In practice and in use, a method for administering intraventricular chemotherapy with an Ommaya reservoir kit may include providing a sterile Ommaya reservoir tray as described herein. The method for administering intraventricular chemotherapy may include removing the retractable winged butterfly needle, such as but not limited to, a 25-gauge butterfly needle, from the kit and positioning it approximately perpendicular to the skin of a patient to access the Ommaya reservoir. A 3-way stopcock may be securely attached to the retractable winged butterfly needle in addition to connecting two luer lock syringes to the 3-way stopcock. Cerebrospinal fluid may be withdrawn via the Ommaya reservoir into the first and second luer lock syringes. The first luer lock syringe may be removed from the 3-way stopcock and replaced with a chemotherapy syringe in an approximately upright position. The 3-way stopcock may be turned to the open position to administer chemotherapy. After administering chemotherapy, the 3-way stopcock may be turned to the off position and the chemotherapy syringe may be removed. A syringe containing preservative free normal saline may be attached to the 3-way stopcock. The 3-way stopcock may be opened such that preservative free normal saline may flush the Ommaya reservoir. Alternatively, after administering chemotherapy, cerebrospinal fluid may be drawn from the ommaya reservoir into the now empty chemotherapy syringe.

Alternatively, the method for administering intraventricular chemotherapy may include removing the retractable winged butterfly needle, such as but not limited to, a 25-gauge butterfly needle, from the kit and positioning it approximately perpendicular to the skin of a patient to access the Ommaya reservoir. A first luer lock syringe may be connected to the retractable winged butterfly needle such that cerebral spinal fluid may be withdrawn. The first luer lock syringe may be removed and replaced with a second luer lock syringe if additional cerebrospinal fluid needs to be drawn. Chemotherapy may be administered in the same way or similar to the methods previously described. A syringe containing preservative free normal saline may be attached to the 3-way stopcock. The 3-way stopcock may be opened such that the preservative free normal saline may flush the Ommaya reservoir.

The methods for accessing an Ommaya reservoir to obtain CSF for diagnostic purposes and/or for administering intraventricular chemotherapy disclosed herein are provided for illustrative purposes and should not be considered limiting. Other methods and procedures for accessing an Ommaya reservoir to obtain CSF for diagnostic purposes and/or for administering intraventricular chemotherapy, including medical institutional policies including variations of the disclosed methods and processes, are contemplated by this disclosure and are considered to fall within the scope of this disclosure.

According to variation 1, an Ommaya reservoir kit may include at least one fenestrated drape; at least one sponge applicator; at least one container of povidone-iodine; at least one retractable winged butterfly needle; at least one luer lock syringe; at least one 3-way stopcock; at least one sealable collection vial; at least one sterile gauze pad; at least one bandage; and a tray constructed and arranged to seat the at least one sealable collection vial in an upright position.

Variation 2 may include the Ommaya reservoir kit as set forth in variation 1, wherein the tray defines at least one indentation constructed and arranged to seat the at least one sealable collection vial in approximately horizontal position and at least one recess constructed and arranged to seat the at least one sealable collection vial in approximately vertical position.

Variation 3 may include the Ommaya reservoir kit as set forth in any of variations 1 through 2 and further may include a paper towel.

Variation 4 may include the Ommaya reservoir kit as set forth in any of variations 1 through 3 wherein the at least one sponge applicator is three sponge applicators.

Variation 5 may include the Ommaya reservoir kit as set forth in any of variations 1 through 4 wherein the at least one container of povidone-iodine is a 0.75 fluid-ounce container of povidone-iodine.

Variation 6 may include the Ommaya reservoir kit as set forth in any of variations 1 through 5 wherein the at least one retractable winged butterfly needle is a 25-gauge by ¾-inch by 12-inch retractable winged butterfly needle.

Variation 7 may include the Ommaya reservoir kit as set forth in any of variations 1 through 6 wherein the at least one luer lock syringe is two 5 cc luer lock syringes.

Variation 8 may include the Ommaya reservoir kit as set forth in any of variations 1 through 7 wherein the at least one sealable collection vial is four 8 cc sealable collection vials.

Variation 9 may include the Ommaya reservoir kit as set forth in any of variations 1 through 8 wherein the tray defines at least four indentations constructed and arranged to seat the four 8 cc sealable collection vials in approximately horizontal positions and four recesses constructed and arranged to seat the four 8 cc sealable collection vials in approximately vertical position.

Variation 10 may include the Ommaya reservoir kit as set forth in any of variations 1 through 9 wherein the at least one bandage is an adhesive bandage.

According to variation 11, a method of accessing an Ommaya reservoir to obtain CSF and/or for administering intraventricular chemotherapy with an Ommaya reservoir kit including a sealed tray constructed and arranged to contain at least one fenestrated drape, at least one sponge applicator, at least one container of povidone-iodine, at least one retractable winged butterfly needle, at least one luer lock syringe, at least one 3-way stopcock, at least one sealable collection vial, and at least one sterile gauze pad, may include the following steps. Opening the sealed tray; opening at least one container of povidone-iodine pouch and pouring the contents of the povidone-iodine pouch into a portion of the tray; utilizing the at least one sponge applicator to cleanse a patients Ommaya reservoir by dipping an applicator sponge in povidone-iodine and cleansing a patients Ommaya reservoir; removing the at least one fenestrated drape from the kit and placing the at least one fenestrated drape over the Ommaya reservoir to create a sterile field over the patient; removing a cap of the at least one sealable collection vial and positioning the at least one sealable collection vial upright in at least one vial indentation defined by the tray; removing the at least one retractable winged butterfly needle from the kit; positioning the at least one retractable winged butterfly needle approximately perpendicular to the skin of a patient to access the Ommaya reservoir; removing the at least one luer lock syringe from the kit; connecting the at least one luer lock syringe to the at least one retractable winged butterfly needle; drawing a volume of CSF from the Ommaya reservoir; and injecting the CSF into the upright at least one sealable collection vial.

Variation 12 may include the method of accessing an Ommaya reservoir to obtain CSF and/or for administering intraventricular chemotherapy with an Ommaya reservoir kit as set forth in variation 11 and may further include removing the at least one 3-way stopcock from the kit; connecting the at least one 3-way stopcock to the at least one retractable winged butterfly; and administering chemotherapy via the Ommaya reservoir.

Variation 13 may include the method of accessing an Ommaya reservoir to obtain CSF and/or for administering intraventricular chemotherapy with an Ommaya reservoir kit as set forth in any of variations 11 through 12 and may further include removing the at least one retractable winged butterfly from the Ommaya reservoir; applying pressure on the Ommaya reservoir with the at least one sterile gauze pad; and applying an adhesive bandage.

According to variation 14, a method of manufacturing an Ommaya reservoir kit may include the steps of providing at least one fenestrated drape; providing at least one sponge applicator; providing at least one container of povidone-iodine; providing at least one retractable winged butterfly needle; providing at least one luer lock syringe; providing at least one 3-way stopcock; providing at least one sealable collection vial; providing at least one sterile gauze pad; providing at least one bandage; providing a tray constructed and arranged to optionally seat the at least one sealable collection vial in an upright position; and sealing the Ommaya reservoir kit.

Variation 15 may include the method of manufacturing an Ommaya reservoir kit as set forth in variation 14, wherein the tray defines at least one indentation constructed and arranged to seat the at least one sealable collection vial in an approximately horizontal position and at least one recess constructed and arranged to seat the at least one sealable collection vial in an approximately vertical position.

Variation 16 may include the method of manufacturing an Ommaya reservoir kit as set forth in any of variations 14 through 15, wherein the at least one sponge applicator is three sponge applicators.

Variation 17 may include the method of manufacturing an Ommaya reservoir kit as set forth in any of variations 14 through 16, wherein the at least one retractable winged butterfly needle is a 25-gauge by ¾-inch by 12-inch retractable winged butterfly needle.

Variation 18 may include the method of manufacturing an Ommaya reservoir kit as set forth in any of variations 14 through 17, wherein the at least one luer lock syringe is two 5 cc luer lock syringes.

Variation 19 may include the method of manufacturing an Ommaya reservoir kit as set forth in any of variations 14 through 18, wherein the at least one sealable collection vial is four 8 cc sealable collection vials.

Variation 20 may include the method of manufacturing an Ommaya reservoir kit as set forth in any of variations 14 through 19, wherein the tray defines at least four indentations constructed and arranged to seat the four 8 cc sealable collection vials in approximately horizontal positions and four recesses constructed and arranged to seat the four 8 cc sealable collection vials in approximately vertical position.

In this disclosure, the descriptions of the various embodiments have been presented for purposes of illustration and are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein. Thus, the appended claims should be construed broadly, to include other variants and embodiments, which may be made by those skilled in the art.

I claim:
1. An Ommaya reservoir kit, comprising:
at least one fenestrated drape;
at least one sponge applicator;
at least one container of povidone-iodine;
at least one retractable winged butterfly needle;
at least one luer lock syringe;
at least one 3-way stopcock;
at least one sealable collection vial;
at least one sterile gauze pad;
at least one bandage; and
a tray constructed and arranged to seat the at least one sealable collection vial in an upright position.

2. The Ommaya reservoir kit as set forth in claim 1, wherein the tray defines at least one indentation constructed and arranged to seat the at least one sealable collection vial in approximately horizontal position and at least one recess constructed and arranged to seat the at least one sealable collection vial in approximately vertical position.

3. The Ommaya reservoir kit as set forth in claim 1, further comprising a paper towel.

4. The Ommaya reservoir kit as set forth in claim 1, wherein the at least one sponge applicator is three sponge applicators.

5. The Ommaya reservoir kit as set forth in claim 1, wherein the at least one container of povidone-iodine is a 0.75 fluid-ounce container of povidone-iodine.

6. The Ommaya reservoir kit as set forth in claim 1, wherein the at least one retractable winged butterfly needle is a 25-gauge by ¾-inch by 12-inch retractable winged butterfly needle.

7. The Ommaya reservoir kit as set forth in claim 1, wherein the at least one luer lock syringe is two 5 cc luer lock syringes.

8. The Ommaya reservoir kit as set forth in claim 1, wherein the at least one sealable collection vial is four 8 cc sealable collection vials.

9. The Ommaya reservoir kit as set forth in claim 8, wherein the tray defines at least four indentations constructed and arranged to seat the four 8 cc sealable collection vials in approximately horizontal positions and four recesses constructed and arranged to seat the four 8 cc sealable collection vials in approximately vertical position.

10. The Ommaya reservoir kit as set forth in claim 1, wherein the at least one bandage is an adhesive bandage.

11. A method of accessing an Ommaya reservoir to obtain CSF and/or for administering intraventricular chemotherapy with an Ommaya reservoir kit including a sealed tray containing at least one fenestrated drape, at least one sponge applicator, at least one container of povidone-iodine, at least one retractable winged butterfly needle, at least one luer lock syringe, at least one 3-way stopcock, at least one sealable collection vial, and at least one sterile gauze pad, comprising:
opening the sealed tray;
opening at least one container of povidone-iodine pouch and pouring the contents of the povidone-iodine pouch into a portion of the tray;
utilizing the at least one sponge applicator to cleanse a patients Ommaya reservoir by dipping an applicator sponge in povidone-iodine and cleansing a patients Ommaya reservoir;

removing the at least one fenestrated drape from the kit and placing the at least one fenestrated drape over the Ommaya reservoir to create a sterile field over the patient;

removing a cap of the at least one sealable collection vial and positioning the at least one sealable collection vial upright in at least one vial indentation defined by the tray;

removing the at least one retractable winged butterfly needle from the kit;

positioning the at least one retractable winged butterfly needle approximately perpendicular to the skin of a patient to access the Ommaya reservoir;

removing the at least one luer lock syringe from the kit;

connecting the at least one luer lock syringe to the at least one retractable winged butterfly needle;

drawing a volume of CSF from the Ommaya reservoir; and injecting the CSF into the upright at least one sealable collection vial.

12. The method of accessing an Ommaya reservoir to obtain CSF and/or for administering intraventricular chemotherapy with an Ommaya reservoir kit as set forth in claim 11, further comprising:

removing the at least one 3-way stopcock from the kit;

connecting the at least one 3-way stopcock to the at least one retractable winged butterfly; and administering chemotherapy via the Ommaya reservoir.

13. The method of accessing an Ommaya reservoir to obtain CSF and/or for administering intraventricular chemotherapy with an Ommaya reservoir kit as set forth in claim 11, further comprising:

removing the at least one retractable winged butterfly from the Ommaya reservoir;

applying pressure on the Ommaya reservoir with the at least one sterile gauze pad; and applying an adhesive bandage.

14. A method of manufacturing an Ommaya reservoir kit, comprising:

providing at least one fenestrated drape;

providing at least one sponge applicator;

providing at least one container of povidone-iodine;

providing at least one retractable winged butterfly needle;

providing at least one luer lock syringe;

providing at least one 3-way stopcock;

providing at least one sealable collection vial;

providing at least one sterile gauze pad;

providing at least one bandage; and providing a tray constructed and arranged to optionally seat the at least one sealable collection vial in an upright position; and sealing the Ommaya reservoir kit.

15. The method of manufacturing an Ommaya reservoir kit as set forth in claim 14, wherein the tray defines at least one indentation constructed and arranged to seat the at least one sealable collection vial in approximately horizontal position and at least one recess constructed and arranged to seat the at least one sealable collection vial in approximately vertical position.

16. The method of manufacturing an Ommaya reservoir kit as set forth in claim 14, wherein the at least one sponge applicator is three sponge applicators.

17. The method of manufacturing an Ommaya reservoir kit as set forth in claim 14, wherein the at least one retractable winged butterfly needle is a 25-gauge by ¾-inch by 12-inch retractable winged butterfly needle.

18. The method of manufacturing an Ommaya reservoir kit as set forth in claim 14, wherein the at least one luer lock syringe is two 5 cc luer lock syringes.

19. The method of manufacturing an Ommaya reservoir kit as set forth in claim 14, wherein the at least one sealable collection vial is four 8 cc sealable collection vials.

20. The method of manufacturing an Ommaya reservoir kit as set forth in claim 19, wherein the tray defines at least four indentations constructed and arranged to seat the four 8 cc sealable collection vials in approximately horizontal positions and four recesses constructed and arranged to seat the four 8 cc sealable collection vials in approximately vertical position.

* * * * *